United States Patent [19]

Sprenger

[11] Patent Number: 5,426,987
[45] Date of Patent: Jun. 27, 1995

[54] APPARATUS FOR COLLECTING SMALL SAMPLES FROM FLOWABLE SOLIDS

[75] Inventor: Glenn R. Sprenger, Louisville, Colo.

[73] Assignee: B3 Systems, Inc., Raleigh, N.C.

[21] Appl. No.: 191,077

[22] Filed: Feb. 1, 1994

[51] Int. Cl.⁶ .................................. G01N 1/04
[52] U.S. Cl. ................................... 73/863.43
[58] Field of Search ........... 73/863.41, 863.43, 863.51, 73/863.52, 863.53, 863.61

[56] References Cited

U.S. PATENT DOCUMENTS

| | | | |
|---|---|---|---|
| 78,009 | 5/1868 | Keller . | |
| 398,275 | 2/1889 | Palmer | 73/863.43 |
| 518,915 | 4/1894 | Clarkson | 73/863.45 |
| 2,405,486 | 8/1946 | Bauer | 73/421 |
| 2,800,797 | 7/1957 | Honstead | 73/421 |
| 4,026,154 | 5/1977 | Pfeiffer et al. | 73/423 R |
| 4,524,628 | 6/1985 | Knudston et al. | 73/863.43 |

FOREIGN PATENT DOCUMENTS

| | | | |
|---|---|---|---|
| 1295132 | 4/1962 | France | 73/863.43 |
| 1049127 | 1/1959 | Germany | 73/863.43 |

Primary Examiner—Hezron E. Williams
Assistant Examiner—Nashmiya Ashraf
Attorney, Agent, or Firm—Sheridan Ross & McIntosh

[57] ABSTRACT

An apparatus for sampling a portion of flowable solid material from a stream thereof is provided. The apparatus includes a plurality of nested stage assemblies enclosed within a housing for sampling successively smaller portions of the solid material flowing therethrough. Each stage assembly includes a conical upper section, a funnel shaped lower section and a substantially cylindrical section disposed therebetween and defining a chamber for receiving a sampled portion of the flowable solid material. Each cylindrical section includes a plurality of openings and removable splitter assemblies for directing the sampled portion into the chamber. Each splitter assembly includes a front wall and opposing side walls defining a mouth for receiving a portion of the flowable solids and flow path through said chute. The front wall widens from the mouth to define flared side walls and an increasing area through which the solid material flows toward the chamber. An outlet tube receives and directs a desired sampled portion of the solid material away from the primary flow.

14 Claims, 5 Drawing Sheets

APPARATUS FOR COLLECTING SMALL SAMPLES FROM FLOWABLE SOLIDS

FIELD OF THE INVENTION

The present invention relates generally to an apparatus for collecting samples from continuous flow processes and more particularly to an apparatus for sampling a small portion of a flowable solid material in a continuous flow process.

BACKGROUND OF THE INVENTION

Numerous reasons may make the ability to accurately obtain a small representative sample of solid materials from a continuous flow process important. For example, the United States Environmental Protection Agency requires certain industries to maintain programs for monitoring various by-products and to demonstrate that the monitoring technology consistently and accurately obtains representative samples from the stream of material. Similarly, a manufacturer's own quality control program may require accurate sampling from a continuous flow process to determine whether the product meets quality standards. To obtain meaningful test results the sampling mechanism must be able to accurately obtain a representative sample of material from a continuous flow process.

In this regard, various devices for collecting a samples of material from a continuous flow process are well known and take numerous embodiments in the art. For example, U.S. Pat. No. 398,275, issued to Palmer, discloses an apparatus for sampling ores including a cone positioned in the flow of the material for directing the flow of material across the surface of the cone and a plurality of splitters for removing a sample of the material. Similarly, U.S. Pat. No. 518,915, issued to Clarkson, discloses a device for sampling flowable solid material from a stream thereof using a series of staged funnels with the lowermost funnel having chutes for removing a portion of the material from the stream.

Numerous other devices for collecting samples from a continuous stream of flowable solids have been disclosed, most of which require positioning within a stream of flowable solids a device having a plurality of chutes for directing a portion of the stream away from the principal flow thereof. However, a common problem with existing sampling devices is the tendency for the flowable solids to block the chutes which direct a sample of material away from the principal material flow. The blocking becomes particularly acute when attempting to sample fine granules or powders, such as cement dust, which exhibit the behavior of sticking to the side walls and sloped floor of the chutes. The geometry of the chutes used with the apparatus frequently contributes to a tendency of particles to build up to the point where they block chutes.

The angle of repose is the maximum angle at which a flowable solid material will remain at rest on a given surface. The angle of repose depends upon characteristics of the flowable solid including the density, the specific gravity, the moisture content, and the particle size distribution. If the sloped floor of the chute is not angled at least equal to or greater than the angle of repose of the material being sampled the material will tend to build up on the floor of the chute causing the chute to become blocked. Additionally, most existing chutes employ straight side walls defining a uniform cross sectional width within the chute. When material begins to build up on the floor of the chute it reduces the cross-sectional area of the exit path, thereby impeding the flow of solids out of the chute and contributing to the blocking of the chute. This blocking may reduce the ability of the device to obtain accurate, reliable samples from the stream. Accordingly, there is a need in the art for a device for accurately and reliably collecting samples from a continuous stream of flowable solids. More particularly, there is a need in the art for a sampling device which is less susceptible to blockage which may hamper the accuracy of the sampling device.

SUMMARY OF THE INVENTION

An object of the present invention is to provide a device for accurately and reliably collecting a sample of a flowable solid material from a continuous flow process.

A further object of the present invention to provide a sampling device which resists blockage caused by the buildup of solids in the chutes which direct the material away from the primary flow.

A further object of the present invention is to provide a sampling device which may be easily adapted to collect samples from a wide variety of materials having different properties.

To accomplish these objectives the present invention employs at least a first stage assembly positionable in the path of the flowable solid having a chamber and a plurality of openings for receiving a portion of flowable solid into the chamber. Each opening has an overlying removable splitter assembly in communication with it for receiving a portion of the flowable solid from a stream thereof and for directing the received portion through the opening into the chamber. Each splitter assembly preferably includes a mouth for receiving the sample of flowable solid and a front wall which preferably increases in width from the mouth, thereby defining an increasing area along which the received portion flows toward the chamber.

More particularly, the first stage assembly may include a substantially conical upper surface positionable transverse to the flow path of the solid material for directing the flow of the solid material across the conical surface and an underlying chamber for receiving a sampled portion of the material. A substantially cylindrical section including a plurality of openings for receiving the sampled portion of the flowable solid material into the chamber is preferably disposed between the upper conical surface and the underlying chamber. First and second channels are preferably disposed adjacent each of the openings.

A plurality of splitter assemblies for removing a portion of the flowable solid material from the stream thereof and for directing the portion through the openings are removably connected with the substantially cylindrical section of the first stage assembly. Each splitter assembly preferably includes first and second webs interconnectable with each of the first and second channels adjacent said openings. Each splitter further preferably includes a chute having a mouth positionable in the flow of the solid material for receiving a portion of the flowing material and at least a front wall and opposing side walls. At least one of the side walls preferably defines a first angle at least equal to, and even more preferably, slightly greater than, the angle of repose of the solid material. The front wall also preferably increases in width from the mouth defining an increasing area along which the sampled portion travels toward the chamber.

The present invention may also include a second stage assembly located in a path of the flowable solid from the first stage assembly and being spaced a sufficient distance from portions of the first assembly to allow solids from the first assembly to mix before contacting the second assembly. The second stage assembly may also include a second substantially conical upper surface positionable in the flow path of the solids from the first stage for directing the flow of the solid material across the conical surface and a second underlying chamber for receiving a sampled portion of the solid material from the first stage. A second substantially cylindrical surface also having a plurality of openings for receiving a sampled portion of the flowable solid material into the second chamber is preferably disposed between the second upper conical surface and the second underlying chamber. A plurality of splitter assemblies are joined to the cylindrical surface over these openings for directing a sampled portion of the solid material from the first stage assembly into the second underlying chamber. The second chamber also includes an outlet for removing the sampled portion of solid material from the flow path of the material.

In one embodiment, the present invention has first and second stage assemblies disposed within a housing adapted for placement in the flow path of the flowable solid. The first stage assembly preferably includes a first conical upper section disposed above a first underlying funnel shaped lower section. A first substantially cylindrical section having a plurality of openings for receiving a portion of the flowable solid into the funnel is preferably disposed between the first upper conical section and the first funnel shaped lower section. The first stage assembly may also include a first cylindrical shell and a first annulus for allowing the flow of the solid material through the housing. Each of the removable splitter assemblies of the first stage assembly is preferably disposed inside of the annulus for directing a portion of the solids flowing through a first annulus into the first chamber.

The second stage assembly is also preferably disposed within the housing in the flow path of solids from the first stage assembly. The second stage assembly is preferably spaced from portions of the first stage assembly at a distance sufficient to allow the solids from the first stage assembly to mix before contacting the second stage assembly. The second stage assembly preferably includes a second conical upper section disposed above a second underlying funnel-shaped lower section. A second substantially cylindrical section having a plurality of openings for receiving a portion of the flowable solids from the first stage assembly into a second chamber is preferably disposed between the upper section and the funnel.

The second stage assembly may also include a second shell and a second annulus for allowing the flow of the solid material from the first stage assembly to pass through the housing. Each of the removable splitter assemblies connected to the second stage assembly is preferably disposed inside of the second annulus for directing a portion of the solids flowing through the second annulus into said second chamber. The second stage assembly also may include an outlet tube exiting the housing from the second chamber for directing the sampled portion of solid material away from the flow of remaining solid material.

DETAILED DESCRIPTION

There is hereinafter described an apparatus for collecting a representative sample of a flowable solid from a stream thereof. The embodiment hereinafter described is particularly adapted for positioning along a substantially vertical axis within a flowable stream of solids. However, it should be appreciated that the present invention could also be adapted for positioning at different angles with respect to the horizontal.

Figure 1:
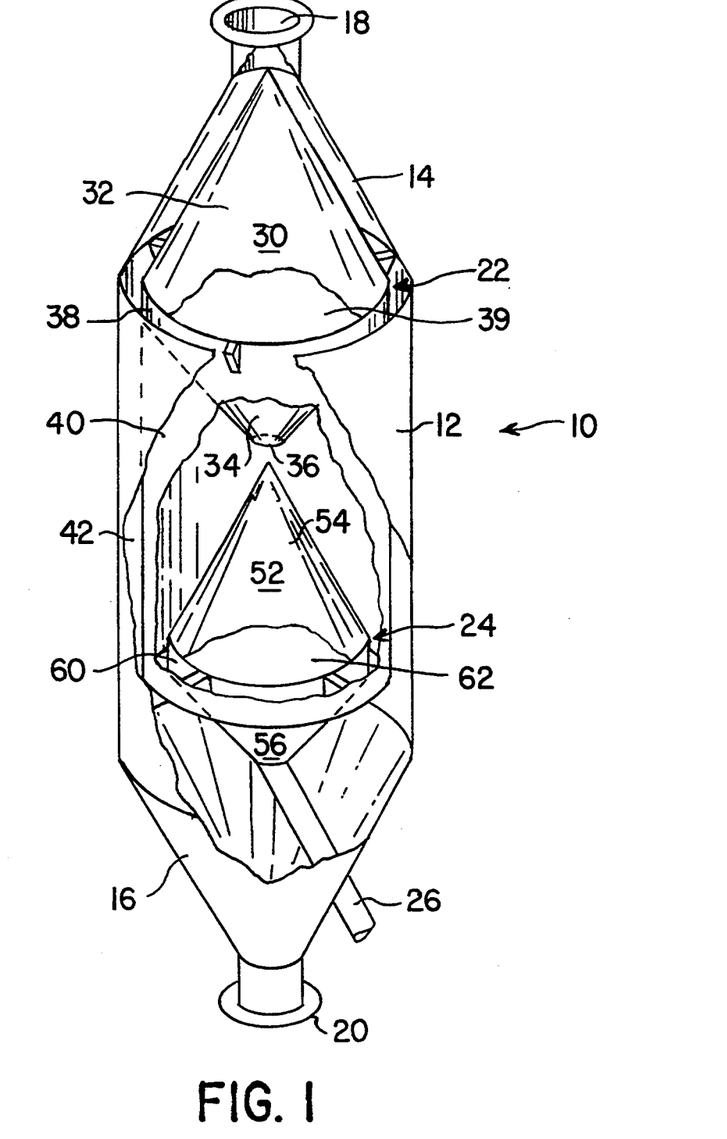
FIG. 1 is a perspective view of one embodiment of the present invention.
Figure 2:
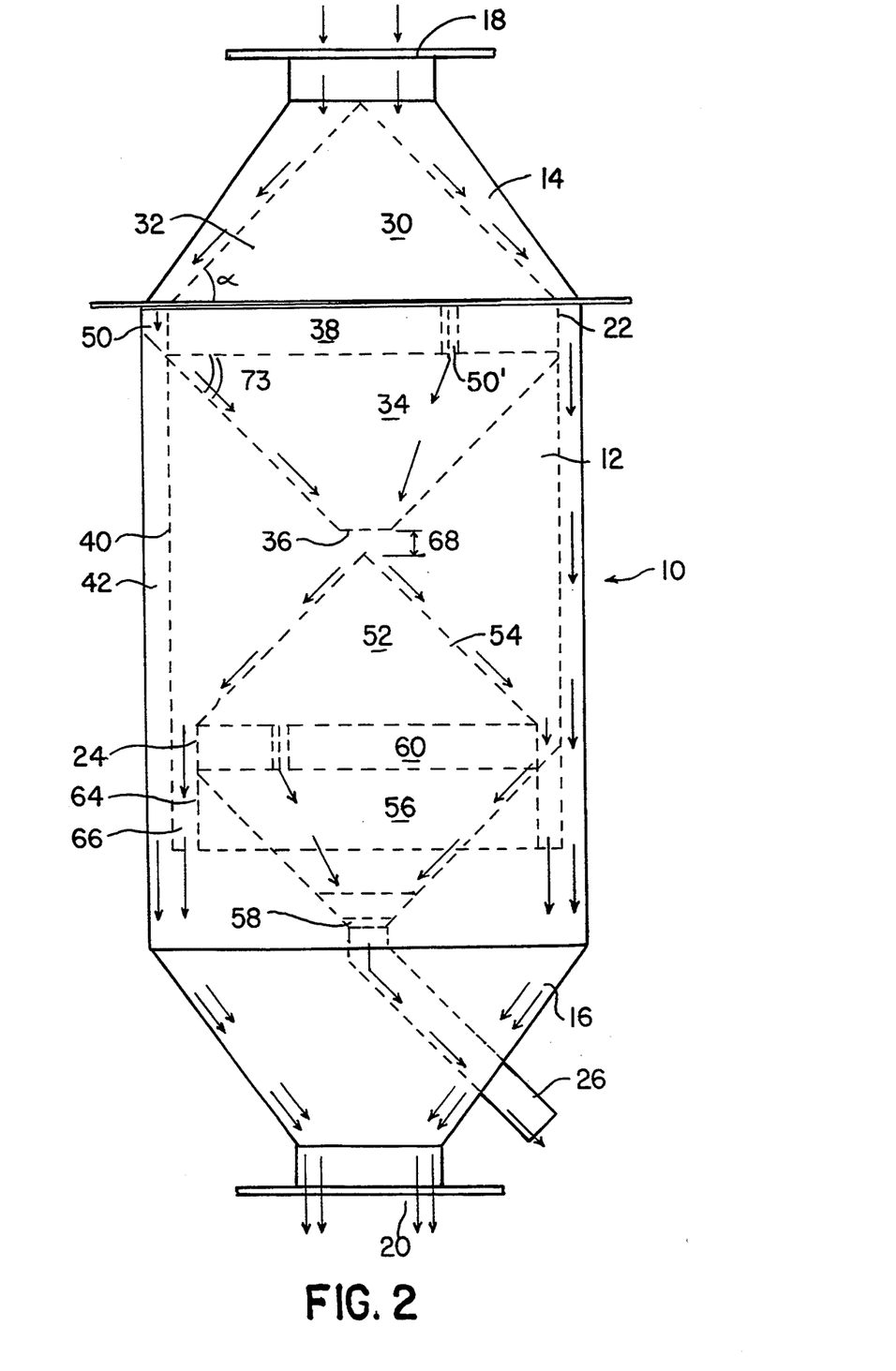
FIG. 2 is a side view of one embodiment of the present invention.

Referring now to FIG. 1 there is shown a perspective view of one embodiment of the present invention in an operating environment. As illustrated in FIGS. 1 and 2, the apparatus includes a first stage assembly 22 and a second stage assembly 24 disposed within a housing 10, however it should be appreciated that more or fewer stage assemblies may be employed depending upon the particular circumstances.

The disclosed housing 10 is particularly adapted for interconnection with a pipe that carries a flowable solid; however, it should be appreciated that the housing may be otherwise adapted for placement within a stream of flowable solids. The housing 10 includes a cylindrical chamber 12 having an upper section 14 and a lower section 16. The housing further includes a first orifice 18 for receiving a stream of flowable solids into the housing 10 and a second orifice 20 for allowing solids to exit the housing 10. A first stage assembly 22 is disposed at the upper end of the housing 10 and a second stage assembly 24 is disposed beneath the first stage assembly 22. An outlet tube 26 for allowing the sampled portion of the flowable solids to exit the housing 10 is also provided.

Referring to FIGS. 1 and 2, it can be seen that the first stage assembly 22 includes an upper section 30 defining a first conical surface 32 and a funnel-shaped lower section 34 having an aperture 36 disposed substantially at the bottom of the funnel-shaped lower section 34. A cylindrical member 38 interconnects the upper and lower sections, thereby defining a first chamber 39 for receiving a portion of the flowable solids. The first stage assembly 22 also includes a first cylindrical shell 40 defining a first annulus 42 through which flowable solids may pass through the housing 10. The first annulus 42 is dimensioned to have a cross-sectional area at least approximately 110% the area of the pipe to which the device is connected and has a minimum width of about one inch.

The apex of the upper section 30 of the first stage assembly 22 is positioned substantially in the center of the material flow to provide for a substantially uniform flow of solids across the surface 32 of the upper section 30. The first conical surface 32 defines an angle, $\alpha$, with respect to the horizontal plane. The embodiment disclosed in FIG. 2 presents an angle, $\alpha$, of approximately 45 degrees with the horizontal, however it should be appreciated that cones having different angles may be used in accordance with the angle of repose of the material being sampled. Similarly, the funnel-shaped lower section 34 presents an angle, $\beta$, with respect to the horizontal. In the embodiment disclosed in FIG. 2, $\beta$ also measures 45 degrees, however it should be appreciated that funnels having different angles may also be used in accordance with the angle of repose of the solids being sampled.

Ideally, the angles $\alpha$ and $\beta$ should be greater than the angle of repose of the material being sampled to inhibit the buildup of material on the conical surface 32 of the upper section 30 and in the funnel-shaped lower section 34. For example, if a solid exhibits an angle of repose of 50 degrees, $\alpha$ and $\beta$ should be approximately 60 degrees. However, design considerations make angles of greater than about 75 degrees impractical. Therefore, materials exhibiting an angle of repose greater than about 70 degrees may require a conventional mechanical vibrator to be affixed to the housing 10 to maintain the flow of material therethrough.

Figure 3A:
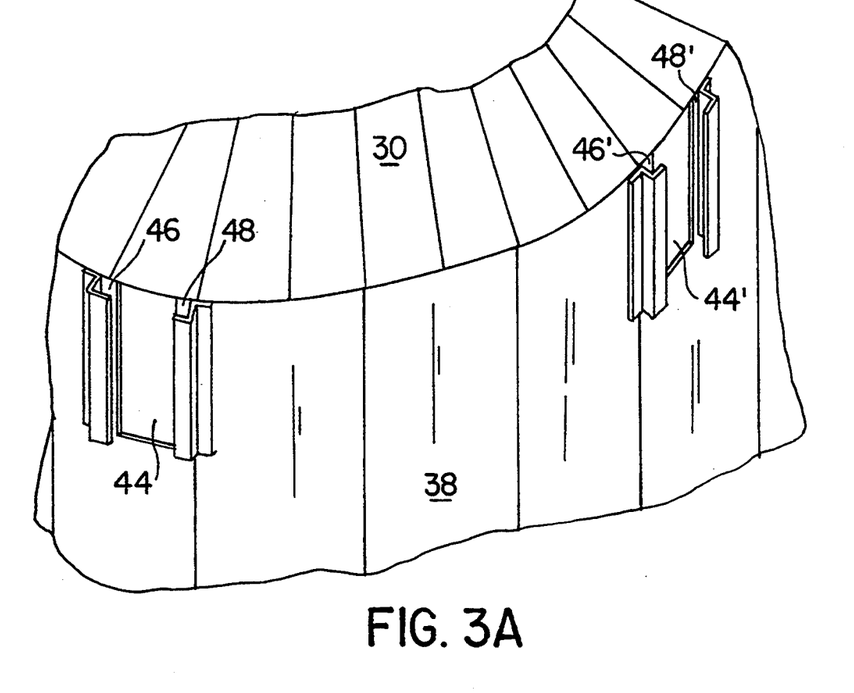
FIGS. 3A–3B are is a perspective views of portions of first and second stage assemblies of the present invention illustrating the openings through which flowable solid material may pass and the adjacent channel members for receiving splitter assemblies.
Figure 4:
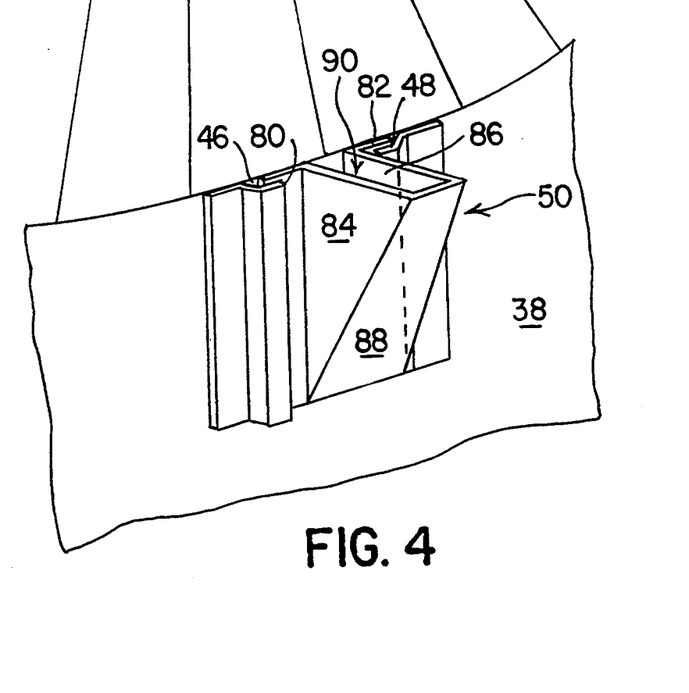
FIG. 4 is a perspective view of a portion of a stage assembly of the present invention illustrating the interconnection of a splitter assembly thereto.

As best illustrated in FIG. 3A, the cylindrical member 38 includes a plurality of openings 44, 44' through which flowable solids may pass into said first chamber 39. Adjacent each opening is a first channel 46, 46' and a second channel 48, 48' for receiving an overlying splitter assembly 50, as seen in FIG. 4. The splitter assemblies 50 are positioned inside of the first annulus 42 to direct a portion of the solids flowing through the first annulus 42 into the first chamber 39. The remainder of the solids flow through the first annulus 42 and exit the device through the second orifice 20 at the lower end of the device.

As seen in FIG. 2, the second stage assembly 24 is positioned beneath the first stage assembly 22 and also includes an upper section 52 defining a conical surface 54 and a funnel-shaped lower section 56 having an aperture 58 disposed at the bottom of the funnel-shaped lower section 56. The cone and funnel angles for the second stage assembly are also determined in accordance with the angle of repose of the flowable solid as discussed above. A cylindrical member 60 interconnects the upper and lower sections, defining a second chamber 62 for receiving a portion of the flowable materials from the first stage assembly 22. The second stage assembly 24 also includes a second cylindrical shell 64 defining a second annulus 66 through which flowable solids from the first stage assembly 22 may pass through the housing 10.

Referring to FIG. 2, it can be seen that the apex of the upper section 52 is positioned substantially in the center of the material flow from the first stage assembly 22 to provide for substantially uniform material flow across the conical surface 54 of the upper section 52. Further, it can be seen that the second stage assembly 24 is positioned a distance 68 from the first stage assembly 22 sufficient to allow the flowable solids to mix before contacting the second stage assembly 24. This distance 68 may vary depending upon the properties of the flowable solid being sampled, the quantity being sampled, and the flow rate.

Figure 3B:
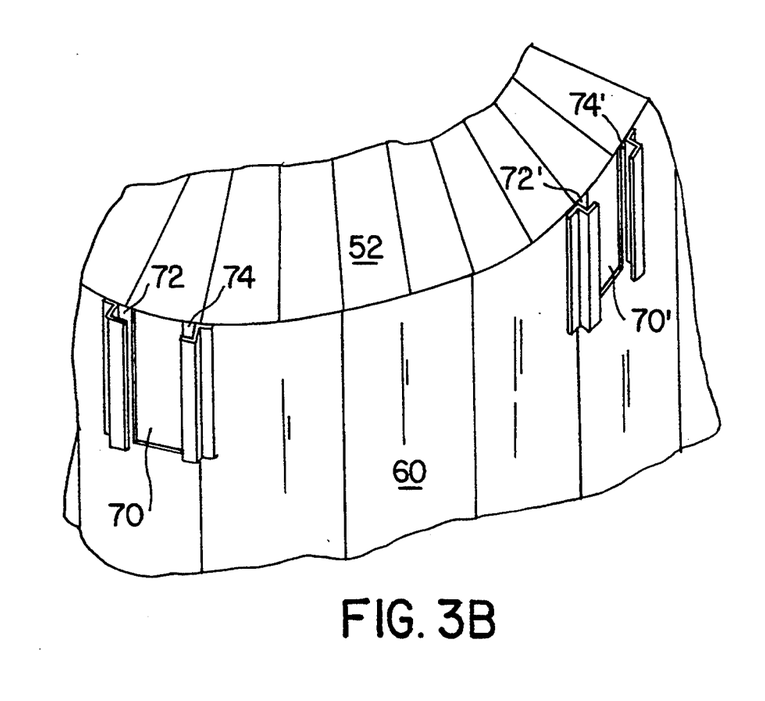

Referring to FIG. 3B, cylindrical member 60 also includes a plurality of openings 70, 70' through which flowable solids from the first stage assembly 22 may pass into the second chamber 62. Adjacent each opening is a first channel 72, 72' and a second channel 74, 74' for receiving an overlying splitter assembly 50. The splitter assemblies 50, as illustrated in FIG. 4, are positioned inside of the second annulus 66 to direct a portion of the solids flowing through the second annulus 66 into the second chamber 62. An outlet tube 26 is disposed at the bottom of the second chamber 62 for directing the solids flowing therethrough out of the housing 10.

Referring now to FIGS. 4–9 the removable splitter assemblies 50 will be described in detail. It should be appreciated that the splitter assemblies 50 are designed to be interchangeable to adapt the apparatus for sampling different materials. Each splitter assembly 50 includes a first web 80 and a second web 82 which are slidably interconnectable with the first and second channels 46, 48, adjacent each opening on the cylindrical members 38, 60. Each chute further includes first and second side walls 84, 86 and a front wall 88 defining a mouth 90 for receiving flowable solids. The width of mouth 90 should be at least three times greater than the diameter of the largest particle being sampled and should not be less than about 0.375 inches.

Figure 7:
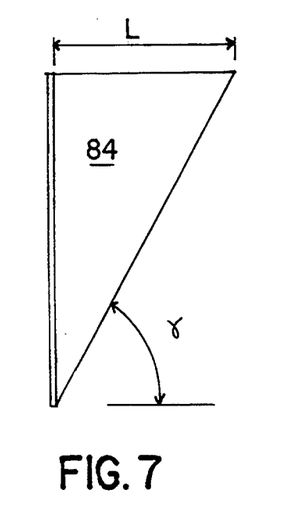
FIG. 7 is a side elevation view of a splitter assembly illustrating a first chute floor angle.
Figure 8:
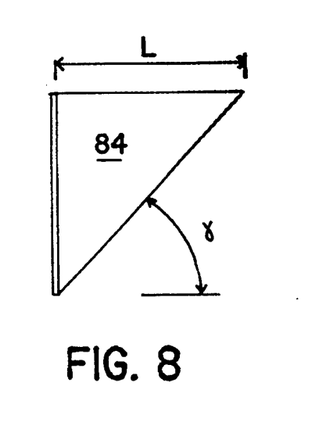
FIG. 8 is a side elevation view of a splitter assembly illustrating a second chute floor angle in which the length of the chute mouth is the same as that illustrated in FIG. 7 and the height of the flared side wall is less than that illustrated in FIG. 7.
Figure 9:
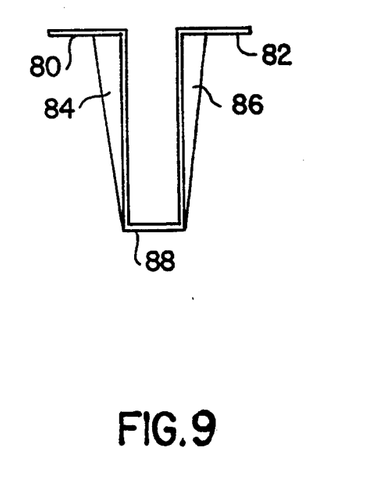
FIG. 9 is a top elevation view of a splitter assembly.

The front wall 88 defines a chute floor angle, $\gamma$, with respect to the horizontal plane. FIG. 7 is a side view of a splitter assembly 50 having a chute floor angle $\gamma$ of approximately 60 degrees and FIG. 8 is a side view of a splitter assembly 50 having a chute floor angle $\gamma$ of approximately 45 degrees. In changing the chute floor angle $\gamma$, the heights of the side walls 84, 86 were reduced in going from the embodiment of FIG. 7 to the embodiment of FIG. 8; while the length of the chute mouth remained the same. The chute floor angle $\gamma$ should be greater than the angle of repose of the material being sampled to facilitate the flow of material through the chute. It has been determined that splitter assemblies having a chute floor angle of not less than about 45 degrees are particularly effective in facilitating the flow of solids through the splitter assembly. Further, it has been determined that design considerations reduce the feasibility of chute floor angles of greater than about 70–75 degrees. Accordingly, it may be necessary to affix a conventional mechanical vibrator to the housing 10 when sampling a solid having an angle of repose greater than about 70 degrees.

Figure 5:
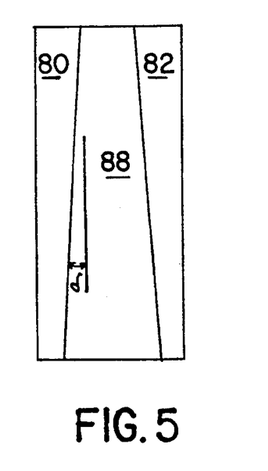
FIG. 5 is a front elevation view of a splitter assembly illustrating a first flared chute wall angle.
Figure 6:
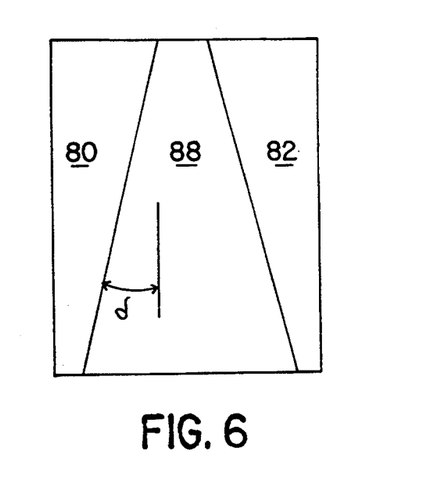
FIG. 6 is a front elevation view of a splitter assembly illustrating a second flared chute wall angle.

Referring now to FIGS. 4, 5, and 6, it can be seen that the front wall 88 is wider at the bottom than the top, defining flared chute side walls having a flare angle sigma ($\sigma$). Flaring the chute's side walls in this manner increases the front wall 88 across which the sampled solid flows toward the chamber defined by the stage assembly, thereby facilitating the flow of solids through the chute. Further, flaring the side walls 84, 86 also reduces the likelihood that the particles will contact or stick to the side walls as they travel through the chute. It has been determined that it is particularly desirable to flare the side walls between 4 degrees for solids with relatively low angles of repose and 14 degrees for solids with relatively high angles of repose. However it should be appreciated that chutes having greater or lesser flare angles are within the scope of the present invention.

In operation the solid to be sampled is tested to determine various characteristics including the particle size range and distribution, the particle density, the bulk density, the moisture content, the temperature and the angle of repose. The process may also be analyzed to assess information such as the size, shape, and material of the process line, the flow rate, the process pressure, and how much room is available for a sampling device. Based on this information a housing may be fitted with stage assemblies having appropriately sloped cones, funnels and chutes. The appropriate number and size of chutes may be connected with the stage assemblies to achieve the desired sampling rate.

After the apparatus is assembled it may be placed within the process flow with the first orifice 18 positioned upstream from the second orifice 20. When the solids enter the apparatus their particles are substantially evenly dispersed across the conical surface 32 of the first stage assembly 22. As the solids flow down the conical surface 32 a portion of the particles enter the mouth 90 of the splitter assemblies 50 attached to the first stage assembly 22. The sampled particles are directed into the chamber 39 of the first stage assembly while the remaining particles flow through the first annulus 42 and exit the device through the second orifice 20.

The sampled particles exit the chamber 39 of the first stage assembly 22 through the aperture 36 at the lower end of the funnel shaped lower section 34. These particles are substantially evenly dispersed across the conical surface 54 of the second stage assembly 24. A portion of these particles are sampled by the splitter assemblies 50 attached to the second stage assembly 24. This sampled portion is directed into the chamber 62 of the second stage assembly 24 and exits the housing 10 through the outlet tube 26. The remaining particles flow through the second annulus 66 and exit the housing 10 through the second orifice 20.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An apparatus for sampling a flowable solid, comprising:
   at least a first stage assembly having a chamber, said first stage assembly including a plurality of sample openings for receiving the flowable solid into said chamber; and
   a plurality of splitter assemblies joined to said first stage assembly and with each of said splitter assemblies overlying one of said sample openings, each of said plurality of splitter assemblies including a top and a bottom,
   a mouth located at a top thereof, with said mouth having a near end adjacent to said first stage assembly and a far end, remote from said first stage assembly and opposite said near end;
   the bottom has a width and said mouth has a width at said near end and in which said width of said bottom is greater than said width of said mouth at said near end;
   an open area that extends at said near end, from said mouth to said bottom;
   a chute front wall that extends from said mouth far end to said bottom with said chute front wall increasing in width in a direction from said mouth to said bottom; and
   first and second chute side walls connected to said chute front wall, each of said first and second chute side walls being inclined outwardly from said mouth, wherein the shortest distance between said first and second side walls at said bottom and at said near end is greater than the shortest distance between said first and second side walls at said mouth and at said near end.

2. An apparatus, as claimed in claim 1, wherein:
said open area is generally trapezoidal in shape at said near end.

3. An apparatus, as claimed in claim 1, wherein:
said first stage assembly includes a cylindrical section and each of said plurality of sample openings is formed in said cylindrical section.

4. An apparatus, as claimed in claim 1, wherein:
each of said splitter assemblies includes first and second webs respectively connected to opposite sides of said first and second side walls and said first stage assembly includes means for removably connecting each of said splitter assemblies thereto.

5. An apparatus, as claimed in claim 4, wherein:
said means for removably connecting includes first and second channel members for receiving said first and second webs.

6. An apparatus, as claimed in claim 1, wherein:
in a front elevation view of each of said splitter assemblies, an angle of at least 4° and no greater than 14° is formed by an edge of said first side wall, that extends from said far end to said bottom, and a vertical line that is perpendicular to said bottom and extends from said first side wall at said far end.

7. An apparatus, as claimed in claim 1, wherein:
in a side elevation view of each of said splitter assemblies, an angle in the range of 45°–75° is formed by an edge of said first side wall that extends from said far end to said bottom and a lateral line that is perpendicular to said bottom.

8. An apparatus, as claimed in claim 6, wherein:
the magnitude of said angle depends upon an angle of repose of the flowable solid.

9. An apparatus, as claimed in claim 1, wherein: said first stage assembly includes an outer shell and a first stage unit disposed within said outer shell and with an annulus being defined between at least portions of said first stage unit and said outer shell and each of said splitter assemblies being located inside of said annulus.

10. An apparatus, as claimed in claim 9, wherein:
said first stage unit includes a cone and a funnel with a cylindrical section interconnecting said cone and said funnel.

11. An apparatus, as claimed in claim 1, further including:
a second stage assembly located in a path of the flowable solid from said first stage assembly, said second stage assembly including a first stage unit being spaced a predetermined distance from said first stage assembly, said predetermined distance being a distance sufficient to allow solids from said first stage assembly to mix before contacting said second stage assembly.

12. An apparatus, as claimed in claim 11, wherein:
said second stage assembly includes a plurality of splitter assemblies with said plurality of splitter assemblies of said second stage assembly being offset from said plurality of splitter assemblies of said first stage assembly.

13. An apparatus, as claimed in claim 1, wherein:
said mouth has a width that is at least one of the following: at least three times greater than the diameter of the largest particle of the flowable solid being sampled and at least 0.375 inch.

14. An apparatus, as claimed in claim 9, wherein:
said annulus has at least one of: a minimum width of at least 1.0 inch and 110% of a cross-sectional area of a pipe to which said first stage assembly is connected.

* * * * *